United States Patent [19]

Maroun

[11] Patent Number: 5,780,027
[45] Date of Patent: Jul. 14, 1998

[54] METHODS OF TREATMENT OF DOWN SYNDROME BY INTERFERON ANTAGONISTS

[75] Inventor: Leonard E. Maroun, Springfield, Ill.

[73] Assignee: Meiogen Biotechnology Corporation, Springfield, Ill.

[21] Appl. No.: 502,519

[22] Filed: Jul. 14, 1995

[51] Int. Cl.$^6$ .......................... A61K 39/395; A61K 38/21
[52] U.S. Cl. ............... 424/130.1; 424/85.4; 424/141.1; 424/143.1; 424/144.1; 424/145.1
[58] Field of Search ........................ 424/130.1, 141.1, 424/143.1, 144.1, 145.1, 85.4

[56] References Cited

U.S. PATENT DOCUMENTS

| | | |
|---|---|---|
| 4,824,432 | 4/1989 | Skurkovich et al. .................. 604/4 |
| 5,297,562 | 3/1994 | Potter .................................. 128/898 |

OTHER PUBLICATIONS

Tan et al., "Human chromosome 21 dosage:effect on the expression of the interferon induced antiviral state", Science, vol. 186, pp. 61–63, Oct. 4, 1974.

Gerders, et al. "Effect of increased gene doage expression on the a–interferon receptors in Down's syndrome", Biochimica et Biophysica Acta, vol. 1181, pp. 135–140, 1993.

Bersu et al., "Altered placental morphology associated with murine trisomy 16 and murine trisomy 19" Teratology, vol. 40 (5), Abstract only, 1989.

Audrius, *J. Neurological Sciences*, 85:209–222 (1988).

Carr, "The Development of Intelligence", *Current Approaches to Down Syndrome*, Ed. Holt et al., 1985, London, pp. 167–186.

Cronk et al., *Pediatrics* 81:102–110 (1988).

Gearhart et al., *Brian Res. Bulletin*, 16:789–801 (1986).

Groner et al., *Journal de Physiologie* 84(1):53–77 (1990).

Gropp et al., *Cytogenet. Cell. Genet.* 13:511–535 (1974).

Haak–Frendscho et al., *Immunology*, 79:594–599 (1993).

Holtzman et al., *EMBO Journal*, 11(2):619–627 (1992).

Kato et al, *Journal of Molecular Neuroscience* 2:109–113 (1990).

Przemioslo et al., *Gut*, 36:874–879 (1995).

Raveendran et al., *P.N.A.S. (USA)* 78(6):3343–3347 (1981).

Wiseman et al., "Interferon and Trisomy 16 Mouse Fetal Heart Development and Function," Abstract #D–1P, The International Conference on Chromosome 21, Mar. 14, 1997, Barcelona, Spain.

Wisniewski et al., "Neuronal Density and Synaptogenesis in the Postnatal Stage of Brain Maturation in Down Syndrome," The Neurobiology of Down Syndrome, ed. Epstein, Raven Press, New York, 1986, pp. 29–44.

Youngman et al., *J. Immunology*, 153:675–681 (1994).

*Primary Examiner*—Sheela Huff
*Assistant Examiner*—Yvonne Eyler
*Attorney, Agent, or Firm*—Pennie & Edmonds LLP

[57] ABSTRACT

The present invention relates to a process for ameliorating or preventing neurological diseases that are caused, in part, by an increased and/or abnormal responsivity to interferon. Down Syndrome (DS) and Alzheimer's Disease (AD) are examples of such diseases. Specifically, the invention provides a method for treating subjects suffering from or at risk for such diseases by the administration of a pharmacological preparation that antagonizes interferon's action.

16 Claims, 5 Drawing Sheets

METHODS OF TREATMENT OF DOWN SYNDROME BY INTERFERON ANTAGONISTS

1. FIELD OF THE INVENTION

The present invention relates to a process for ameliorating or preventing neurological diseases that are caused, in part, by an increased and/or abnormal responsivity to interferon. Down Syndrome (DS) and Alzheimer's Disease (AD) are examples of such diseases. Specifically, the invention provides a method for treating subjects suffering from or at risk for such diseases by the administration of a pharmacological preparation that antagonizes interferons' action.

2. BACKGROUND OF THE INVENTION
2.1. THE MOLECULAR BIOLOGY OF INTERFERONS AND INTERFERON RECEPTORS

Interferons are proteins that alter and regulate the transcription of genes within a cell by binding to interferon receptors on the regulated cell's surface and thus prevent viral replication within the cells. There are five types of interferons (IFN), which are designated $\alpha$ (formerly $\alpha_1$), $\omega$ (formerly $\alpha_2$), $\beta$, $\gamma$ and $\tau$. Mature human interferons are between 165 and 172 amino acids in length. In humans IFN-$\alpha$ and IFN-$\omega$ are encoded by multiple, closely related non-allelic genes. Additionally, there are pseudo-genes of IFN-$\alpha$ and IFN-$\omega$. By contrast, IFN-$\beta$ and IFN-$\gamma$ are encoded by unique genes.

The interferons can be grouped into two types. IFN-$\gamma$ is the sole type II interferon; all others are type I interferons. Type I and type II interferons differ in gene structure (type II interferon genes have three exons, type I one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each others binding to cellular receptors, while type II interferon has a distinct receptor. Reviewed by Sen, G. C. & Lengyel, P., 1992, J. Biol. Chem. 267:5017–5020.

Although all type I interferons compete for binding to a common receptor or receptors, the effects of different type I interferons can be different. Pontzer, C. H., 1994, J.Interfer.Res. 14:133–41. Additionally, there appears to be several kinds of type I interferon receptor. For example, there is evidence that the type I interferon receptors of different cell types are different. Benoit, P., 1993, J. Immunol. 150:707. The number of genes encoding the type I interferon receptors is unknown; however, the genes appear to be linked to each other and to at least one gene encoding an IFN-$\gamma$ receptor component as well. In humans, chromosome region 21q21.1–21.31 encodes all the genes needed for the receptor for type I interferon (Raziuddin, A., 1984, Proc. Natl. Acad. Sci. 81:5504–08; Soh, J., 1993, Proc. Natl. Acad. Sci. 90:8737–41; Soh, J., 1994, J. Biol. Chem. 269:18102–10) and at least one essential component of the type II interferon receptor (Jung, V., 1990, J. Biol. Chem. 265:1827–30).

2.2. THE BIOLOGY OF INTERFERON ACTION AND DOWN SYNDROME

The binding of interferons to their receptor, leads to a cascade post-translational modification to other proteins which are then transported to the nucleus where they regulate the transcription of genes by binding to specific nucleic acid sequences. The nucleic acid sequence which is characteristic of genes responsive to type I interferons is designated the Interferon Sensitive Response Element (ISRE). Reviewed Tanaka, T. & Taniguchi, T., 1992, Adv. Immunol. 52:263. Type-I interferons are synthesized in response to viral infection, except for IFN-$\tau$ which is constitutively produced in the placenta; Type II interferons are synthesized in response to antigen stimulation.

Interferons alter the rates of synthesis and the steady state levels of many cellular proteins. An overall effect of interferon is usually an inhibition of cellular proliferation.

The possibility that cells from subjects having Down Syndrome may have abnormal responsivity to interferon was introduced by the discovery that a gene encoding an interferon inducible protein, which was subsequently identified as the type I interferon receptor, was located on chromosome-21. Tan Y. H. et al., 1974, J. Exp. Med. 137:317–330. This observation prompted comparisons of the response of diploid and trisomy-21 aneuploid cultured cells to interferon added to the culture medium. These studies have consistently shown an increased responsivity of trisomy-21 cells to interferon. Tan, Y. H., et al., 1974, Science 186:61–63; Maroun, L. E., 1979, J. Biochem. 179:221; Weil, J., et al., 1983, Hum. Genetics 65:108–111; reviewed Epstein, C. J., & Epstein, L. B., 8 LYMPHOKINES pp277–301 (Academic Press, New York, 1983); Epstein, C. J. et al., 1987, ONCOLOGY AND IMMUNOLOGY OF DOWN SYNDROME (Alan R. Liss, 1987). The publications of these studies have been accompanied by speculative conjectures that the altered responsivity to interferon played a role in the pathogenesis of lesions of Down Syndrome. See, Maroun, L. E., 1980, J. Theoret. Biol. 86:603–606.

2.3. DOWN SYNDROME AND ANIMAL MODELS OF IT

An animal model of Down Syndrome has been constructed by use of the knowledge that human chromosome-21 is syntenic to mouse chromosome-16, i.e., that many of the genes present on each are homologs of each other. Mice having specified trisomies can be bred by use of parental mice having "Robertsonian" chromosomes, i.e., chromosomes that are essentially the centromeric fusion of two different murine chromosomes. A variety of such Robertsonian chromosomes have been identified, including at least two involving chromosome-16 and a second different chromosome: Rb(16.17) and Rb(6.16). Mice homozygous for any Robertsonian or combination of independent Robertsonian chromosomes are euploid and fertile.

The intercross ($F_1$) between an Rb(16.17) and an Rb(6.16) mouse is also fully diploid at each genetic locus, although errors in meiosis may cause reduced fertility. Note that in such an $F_1$ both the maternal and paternal chromosome-16 are a part of a Robertsonian chromosome.

Because of meiotic errors the outcross between a mouse having both two different Robertsonian chromosome-16's and a non-Robertsonian mouse gives rise to a trisomy-16 conceptus in between 15% and 20% of cases. Gearhart, J. D., et al., 1986, Brain Res. Bull. 16:789–801; Gropp, A., et al., 1975, Cytogenet. Cell Genet. 14:42–62. The murine trisomy-16 fetuses develop to term but do not live beyond birth by more than a few hours.

Examination of the fetal trisomy-16 and the post-partum human trisomy-21 reveals a number of analogous or parallel lesions. For this reason, the murine trisomy-16 construct is considered to be an animal model of Down Syndrome. Epstein, C. J., THE METABOLIC BASIS OF INHERITED DISEASE, 6TH ED. pp291–326 (McGraw-Hill, New York, 1989); Epstein, C. J., et al., 1985, Ann. N.Y. Acad. Sci. 450:157–168. Because a murine trisomy-16 fetus is not viable post partum, the opportunity to study the neurological pathology of the model has been limited. However, it is clear that in both human trisomy-21 and murine trisomy-16 there is an overall reduction in fetal size and particularly in the development of the fetal brain. Epstein, C. J., THE CONSEQUENCES OF CHROMOSOME IMBALANCE: PRINCIPLES, MECHANISMS AND MODELS (Cambridge University Press, New York, 1986). Further insights into the effects of murine trisomy-16 have been obtained by the formation of Ts16←→2N chimeras (Gearhart, J. D., et al., 1986, Brain Res. Bulletin 16:815–24) and by transplantation of fetal-derived Ts16 tissue into a 2N host (Holtzman, D. M., et al., 1992. Proc. Natl. Acad. Sci. 89:138387; Holtzman, D. M., et al., DOWN SYNDROME AND ALZHEIMER DISEASE, pp227–44 (Wiley-Liss, New York, 1992).

2.4. ALZHEIMER'S DISEASE AND AMYLOID PRECURSOR PROTEIN

Alzheimer's Disease is a progressive dementia which is characterized by the precipitation of a peptide, termed an $A\beta$ peptide, of about 40 amino acids within the brain and within the walls of blood vessels in the brain. The $A\beta$ peptide is derived from the processing of a larger cell surface protein called the $\beta$ Amyloid Precursor Protein ($\beta APP$). Production of the $A\beta$ peptide is not per se pathological. The functions of both the $A\beta$ peptide or $\beta APP$ are unknown.

Several lines of evidence indicate that the deposition of the $A\beta$ peptide is not merely correlative but rather causative of Alzheimer's Disease. The gene encoding $\beta APP$ is located on chromosome-21 and, as noted above, subjects having Down Syndrome develop Alzheimer's Disease. More directly, kinship groups have been identified among the many causes of familial Alzheimer's Disease in which the inheritance of the Disease is linked to the inheritance of a gene encoding a mutated $\beta APP$, moreover the mutation is within the $A\beta$ peptide itself. Reviewed Selkoe, D. J., 1994, Ann. Rev. Neurosci. 17:489–517. Transgenic mice, having multiple copies of such a mutant $\beta APP$ gene, operatively linked to a strong, neuronal and glial cell specific promoter, develop the anatomical lesions of Alzheimer's Disease at about 6–9 months of age. Games, D., et al., 1995, Nature 373:523.

There is a relationship between Down Syndrome and Alzheimer's Disease. The gene encoding the $\beta APP$ is found on chromosome-21. Patients with Down Syndrome are at increased risk of developing Alzheimer's Disease, most often by about the fifth decade of life although cases of earlier development have been reported. Mann, D. M. A., et al., 1990, Acta Neuropathol. 80:318–27.

3. SUMMARY OF THE INVENTION

The present invention is based, in part, on the recognition that in certain pathologic processes that result in mental impairment, the host is rendered abnormally and/or aberrantly sensitive to the effects of interferon so that the effects of interferon become an immediate and direct cause of the pathology. Such processes include, in humans, trisomy of chromosome-21 or the portion of the chromosome-21 that encodes the receptor for type I interferon and at least one component of the receptor for IFN-γ, which is the genetic abnormality associated with Down Syndrome; and also include Alzheimer's Disease.

The present invention provides a method of ameliorating the pathologic effects of interferon by administering to a subject, in the above-noted circumstances, an antagonist of interferon. Embodiments of the invention include the administration of antagonists, alone or in combination, that are antagonists of Type I interferon, Type II interferon (IFN-γ), and placental interferon (IFN-τ).

4. DESCRIPTION OF THE FIGURES

FIG. 1A–1C. The lengths of Trisomy 16 fetuses plotted as a function of the average length of normal littermates. FIG. 1C, anti-IFN injected fetuses. An analysis-of-covariance was performed to compare the groups on length while adjusting for average normal littermate length. The lengths of the anti-IFN treated group were significantly greater than those of the ns-IgG injected controls (p=0.0112) and those of the uninjected controls (p=0.0037). The dotted lines in each figure encompass the 95% confidence limits.

FIG. 2A–2B. Morphometric analysis of the development in normal, Trisomy 16 treated and Trisomy 16 sham treated fetuses.

5. DETAILED DESCRIPTION OF THE INVENTION

5.1. SELECTION OF SUBJECTS

The present invention concerns the administration of interferon antagonists to subjects in order to ameliorate the neurological and developmental abnormalities in the subject due to the action of interferon. A particular group of subjects at risk are subjects having a trisomy of the portion of the chromosome region, designated in humans 21q21.1–21.31, that encodes for interferon receptors. This group has the clinical diagnosis of Down Syndrome. Grete, N., 1993, Eur. J. Hum. Genetics 1:51–63; Sinet, P. M., 1994, Biomed. & Pharmacol. 48:247–252. The homologous chromosome in mice is chromosome-16.

Diagnosis of Down Syndrome can be made by any method known to the medical arts. Typically, for diagnosis in utero, amniocentesis can be performed at about 14 weeks of gestational age and chorionic villus sampling (biopsy) can be performed between 9 and 12 weeks of gestational age. Down Syndrome in children and adults is diagnosed from karyotypes of peripheral blood cells. Cells from either type of sample are cultured and cytogenetic examination can be performed by methods well understood by those skilled in the art.

As noted above, subjects having Down Syndrome are at increased risk to develop Alzheimer's Disease. A further group of subjects that would benefit from the invention consist of subjects having the diagnosis of probable Alzheimer's Disease or who are at increased risk of developing Alzheimer's Disease from causes other than Down Syndrome. The diagnosis of probable Alzheimer's Disease is made by clinical criteria (McKhann, G., 1984, Neurology 34:939; DIAGNOSTIC AND STATISTICAL MANUAL OF MENTAL DISORDERS IV, American Psychological Association, Washington, D.C.). Persons having a familial predisposition to Alzheimer's Disease are also suitable subjects for the present invention.

5.2. THE SELECTION OF ANTAGONISTS

The antagonist of the invention can be any antagonist that can be administered to the subject in an amount effective to prevent the deleterious action of the interferon on the central nervous system.

The effective amount of antagonists that act by binding to and blocking interferon proteins in the blood can be determined by assaying the concentration of bioavailable interferon in the subjects blood. An effective dose of antagonist is a dose that is sufficient to reduce the level of bioavailable interferon by between at least three to five fold, more preferably by about ten fold and most preferably by about twenty five fold below the normal levels of interferon.

The assay of bioavailable interferon is performed by adding a sample of the subjects blood to a culture of an interferon sensitive cell line which is then infected with a test virus, typically Vesicular Stomatitis Virus (VSV), and the number of viral plaques is determined or the cytotoxic effects of the VSV infection is otherwise quantitated. Bioavailable interferon blocks productive viral infection. The level of bioavailable interferon is calculated by comparing various dilutions of the test sample with a titration of a standard sample of interferon. Such assays are rountine in the art. See, e.g., Hahn, T., et al., 1980, in INTERFERON: PROPERTIES AND CLINICAL USES, ed. by A. Khan, N. O. Hill and G. L. Dorn, (Leland Fikes Foundation Press, Dallas, Tex.); Armstrong, J. A., 1971, Applied Microbiology 21:723–725; Havell, E. A. & Vilcek, J. 1972, Anti-microbial Agents and Chemotherapy 2:476–484.

In one embodiment of the invention the antagonist is a monoclonal anti-interferon antibody or fragment thereof. The production of such antibodies is well known in the art. The production of anti-IFN-α monoclonal antibodies that block interferon activity is taught by U.S. Pat. No. 4,973,556 to Bove et al. The production of blocking monoclonal antibodies to IFN-γ is taught by U.S. Pat. No. 4,948,738 to Banchereau. The structure of human trophoblastic interferon (IFN-τ) has been recently disclosed (Whaley, A. E., 1994, J. Biol. Chem. 269:10864–8). Monoclonal antibodies and other antagonists to this interferon can be produced using methods well known to those skilled in the art.

In a preferred embodiment, the antibody is a "chimeric" antibody, i.e., an antibody having a variable region from one species and a constant region from another species. Most typically chimeric antibodies for use in humans have constant regions of human origin. In an alternative preferred embodiment, the antibody is a "grafted" antibody, i.e., an antibody having complementarity determining regions from one species and a constant region and a framework region of the variable region from a second species. A grafted antibody in which the second species is human is termed a "humanized" antibody. Methods of making chimeric antibodies suitable for pharmaceutical use are disclosed in patent publication WO92/16553 by Le, J. (Oct. 1, 1992). "Grafted" antibodies and "humanized" antibodies are described in U.S. Pat. No. 5,225,539 to Winter and patent publications WO91/09967 and WO92/11383 by Adair, J. R. et al. Suitable antagonists, smaller than an antibody molecule, can be derived from anti-interferon monoclonal antibodies by techniques well known in the art. See, e.g., U.S. Pat. No. 5,091,513 to Huston and U.S. Pat. No. 5,260,203 to Ladner. As used herein the term "antibody antagonists" includes natural polyclonal and monoclonal antibodies, chimeric and grafted antibodies, and enzymatically and recombinantly produced interferon binding fragments of each type of antibody.

In an alternative embodiment the antagonist can be a recombinantly produced protein that comprises the interferon binding portion of an interferon receptor. The production of soluble interferon receptors by baculovirus transduced cells is described in Fountoulakis et al., 1991, Eur. J. Biochem. 198:441–450. Alternatively the antagonist can be a fusion protein that contains an interferon binding domain of an interferon receptor.

In alternative embodiments, the antagonist can be an antibody to an interferon receptor, a soluble interferon receptor, receptor fragment, or a peptide that is derived from an interferon that occupies the receptor binding site but does not activate the receptor. Such an IFN-γ peptide antagonist is disclosed by Jarpe, M. A. et al., 1993, J. Interferon Res. 13:99–103.

When the subject is a fetus, or an infant less than 6 weeks of age, the blood brain barrier is not fully formed. In these circumstances antibodies and other proteins that block the interferon receptor can directly reach the central nervous system. When the subject has an intact blood brain barrier, the preferred embodiment of the invention employs antibodies and proteins that block interferon by binding the interferon directly, rather than those that act at the interferon receptor.

Alternatively, increased CNS entry of antibody antagonists can be obtained by chemical modification of the antagonist. Such modifications include cationization, Pardridge, W., 1991, "Peptide Drug Delivery to the Brain", and glycation, Poduslo, J. F., & Curran, G. L., 1994, Molecular Brain Research 23:157.

The interferon antagonist can be a mixture of antagonists that are specific for the various different types of interferon. When one type of interferon predominates, the antagonist can be an antagonist for only the predominate type of interferon that is present. For example, when the subject is a fetus, the antagonist can be a INF-τ specific antagonist.

When the subject is a fetus, then the antagonist can be administered by a transplacental route, e.g., antibody that is transported across the placenta. The human isotypes IgG1, IgG3 and IgG4 are suitable for transplacental administration.

5.3. SELECTION OF DOSE AND TIMING OF ADMINISTRATION

The amount of an antibody antagonist administered is between 1 and 100 mg/kg. The preferred route of administration of an antibody antagonist is intravenous administration to infant and adult subjects. The preferred route of administration to fetal subjects is by intravenous administration to the mother followed by transplacental transport. Alternatively antibody antagonists can be administered by intramuscular and subcutaneous routes. When an antagonist is delivered transplacentally, the calculation of the dose is based on the maternal weight.

The antagonist is administered to subjects having Down Syndrome preferably at the time when the central nervous system is developing most rapidly. The preferred period of administration is from a gestational age of 24 weeks onwards until a post natal age of about 2 years. Even though some proliferation of neurons takes place during weeks 8–18, it is not critical that an antagonist be administered to a human subject prior to week 20–24 of gestational age because the synaptic connections between the neurons are not formed until week 20. Brandt, I., 1981, J. Perinat. Med. 9:3. The administration of the antagonist to subjects having Alzheimer's Disease should commence at the time that the diagnosis of probable Alzheimer's Disease is first made and continue there after. In middle age, subjects having Down Syndrome develop a dementia having an anatomical pathology which is identical to Alzheimer's Disease (Mann, D. M. A., 1988, Mech. Aging and Develop. 43:99–136). Thus, the administration of the antagonist to Down Syndrome patients can be continued throughout the life of the patient, as Down Syndrome patients are at risk for Alzheimer's Disease ab initio.

The frequency of administration is determined by the circulation time of the antagonist, which can be determined by direct measurement by methods well known to those skilled in the art.

In an alternative embodiment of the invention, the administration of interferon antagonists is replaced by the extracorporeal treatments of the subject's blood to remove circulating interferon, such as is described in U.S. Pat. No. 4,605,394.

5.4. A MODEL EMBODIMENT OF THE INVENTION

The invention is exemplified and its operability is demonstrated by the experiments that are presented in Example 1 below. Briefly, normal female mice were crossed with double heterozygous males having Rb(6.16) and Rb(16.17) chromosomes. The females were injected with a mixture of rat monoclonal anti-IFN-γ (1500 neutralizing units) and rabbit polyclonal anti-IFN-α/β (1362 neutralizing units) interperitonally (i.p.) on days 8, 10, 12 and 14 of pregnancy. On day 17 the embryos were biopsied for cytogenetic classification, sacrificed and four gross parameters were measured and compared to the genetically normal littermates in order to assess relative development. Control groups consisted of untreated females and sham treated females which were given normal rabbit and rat serum γglobulin injections.

The four measured parameters were overall (crown-rump) length of the fetus, shape of the back (normally concave at birth), eye-closing (the eyes normally close shortly before birth) and fetal weight. The results of the comparison of each of the parameters from 17 untreated, 16 sham treated and 18 treated controls showed a statistically significant reduction in the growth retardation/maturation of the treated trisomy-16 fetal mice compared to their euploid littermates.

The fetuses from anti-IFN treated mothers had a mean weight decrease of $-10.92\%$ compared to a $-21.47\%$ decrease for the uninjected group (p=0.079) and a $-30.46\%$ decrease for the ns-IgG injected group (p=0.0003) relative to diploid littermates. The uninjected and ns-IgG injected control groups were not statistically different from each other (p=0.174).

6. EXAMPLE TREATMENT OF MURINE TRISOMY-16 BY A INTERFERON ANTAGONIST

6.1. MATERIALS AND METHODS

Animals and Mating. 6:16 Robertsonian translocation male (Rb[6.16]24Lub) and 17:16 Robertsonian translocation female (Rb[16.17]7Bnr) homozygotes were purchased from Jackson Laboratories, Bar Harbor, Me. Mature (54 day) male offspring of these homozygotes (double heterozygotes) were mated to 8–10 wk old euploid, nulliparous, C3H/HeJ females (Jackson Laboratories). Surgery was performed on day 17 or 18 to yield fetuses at the 17–25 mm stage (Theiler, K. (1972) In: *The House Mouse*, Springer, Berlin, Heidelberg, N.Y.). The last three days of gestation are when the morphologic characteristics (eye closure, back curvature and accelerated growth) can be quantified.

Injections. Intraperitoneal (IP) injections (0.25 cc) were begun on post-coitus day 8 (implantation occurs on day 5.5). Injections were given every 48 hours for a total of four injections per animal.

Rabbit polyclonal anti-mouse α/β IFN purified IgG (970 neutralizing units/mg of protein, cat.#25301), and rat monoclonal IgG1 anti-mouse γ IFN, (7,200 neutralizing units/mg, cat. #25001) were obtained from Lee Biomolecular Research Incorporated, San Diego, Calif. The anti-IFNs (supplied lyophilized from saline) were dissolved in sterile water-for-injection (Investage) at a concentration that would deliver 1500 neutralizing units of anti-γ and 1362 neutralizing units of anti-α/β IgG per injection. The expectation was that the IgG would reach the developing fetus through active IgG placental transfer (Guzman-Enriques, L., et al., 1990. J. Rheumatol., 17:52–56). Control injections delivered the same mg quantities of rat (Pierce cat. #31233X) and rabbit (Pierce cat. #31207X) non-specific IgGs in an equivalent volume of sterile saline-for-injection (Abbott). A second control group consisted of uninjected mothers which were left undisturbed.

Fetus Processing. Fetuses, obtained by hysterectomy of mice sacrificed by cervical dislocation, were photographed, measured and fixed whole in Bouins fixative (Luna, L. G. (1968) In: *Manual of Histologic Staining Methods of the Armed Forces Institute of Pathology*, (3rd edition), The Blakiston Division, McGraw-Hill Book Company, New York). Prior to fixation, limb tissue was obtained and minced to provide fibroblast cultures for karyotyping. The fetal fibroblasts from the minced tissue were grown at 37° C. in EAGLE's Minimum Essential Media containing 20% fetal bovine serum, 2 mM glutamine, 100 units/ml of penicillin, and 100 µg/ml of streptomycin. After five days in culture, colchicine (Sigma) was added to level of 1 µg/ml. One hour later, cells were collected, swelled in 25% media, and fixed in fresh methanol: acetic acid (3:1). Crown- to-rump length was measured immediately after the fetus was obtained by measuring the vertex-to-rump distance (without pressure on the fetus) while the fetus was floating in serum-free Minimum Essential Media. Except where otherwise noted, all statistical analyses were done using a two-tailed student's T-test.

6.2. RESULTS AND DISCUSSION

Mice pregnant with trisomy 16 conceptuses were obtained by the mating of euploid nulliparous C3H/HeJ females with doubly heterozygous males. The males were also functionally euploid (i.e., they have a total of 40 chromosome arms) but they carried two Robertsonian translocation chromosomes (6.16 and 17.16), each with one chromosome #16 arm. The meiotic misdistribution of these translocation chromosomes results in a high frequency of trisomy 16 fetuses carrying a maternal acrocentric chromosome 16 and both paternal translocation pseudometacentric chromosomes. This genetic system has been described in detail (Gropp, A., et al., 1975, Cytogenet. Cell Genet. 14:42–62; Gearhart, J. D., et al., 1986, Brain Res. Bull. 16:789–801). Anti-IFN treated mothers received four IP injections of a cocktail of anti-α, β and γ IFN immunoglobulins. One control group of mothers was left unhandled and one was given comparable injections of non-specific IgG.

Mechanisms for the transfer of the IgG from mother-to-fetus and neonate vary widely from species to species. Generally, some combination of passive and active transport is involved; sequentially utilizing the yolk sac and placenta prior to birth, and the intestine postnatally. In the mouse system, maternal antibodies can initially be found in the fluid filling the blastocyst cavity (Brambell, F. W. R., 1966, The Lancet 7473). This may be due simply to passive diffusion, as this fluid generally resembles dilute maternal blood plasma. Shortly thereafter active transport of IgG class immunoglobulins via Fc receptors becomes primarily the function of the yolk sac. This function is later shared but, in rodents, never dominated by Fc mediated transfer of IgG across the placenta (Roberts, D. M. et al., 1990, J. Cell Biol. 111:1867–1876). In the experiments presented here, mice were injected after day 5.5 because of the possibility that trophoblast interferon may play an important role at implantation (Roberts, R. M., 1991 BioEssays 13:121–126). In the mouse, injected polyclonal rabbit IgG has an expected half-life of approximately 5 days (Spiegelberg, H. L. & W. O. Weigle, 1965, J. Exp. Med. 121:323–337).

A total of 68 late stage fetuses with abnormal morphology were obtained from among 440 offspring of 143 doubly heterozygous male×C3H/HeJ female matings. Only fetuses that were both successfully karyotyped and from litters where euploid fetuses averaged greater than 17 mm in length (crown-to-rump |CRL|) are included in TABLE 1 and in all graphs. Fifty-one of a total of 68 trisomies met these criteria. In all cases, the return-toward-normal values are seen with or without the inclusion of unkaryotyped fetuses. For comparison, p values calculated with the unkaryotyped fetuses included are provided in brackets next to those calculated using only successfully karyotyped fetuses.

Figure 1A:
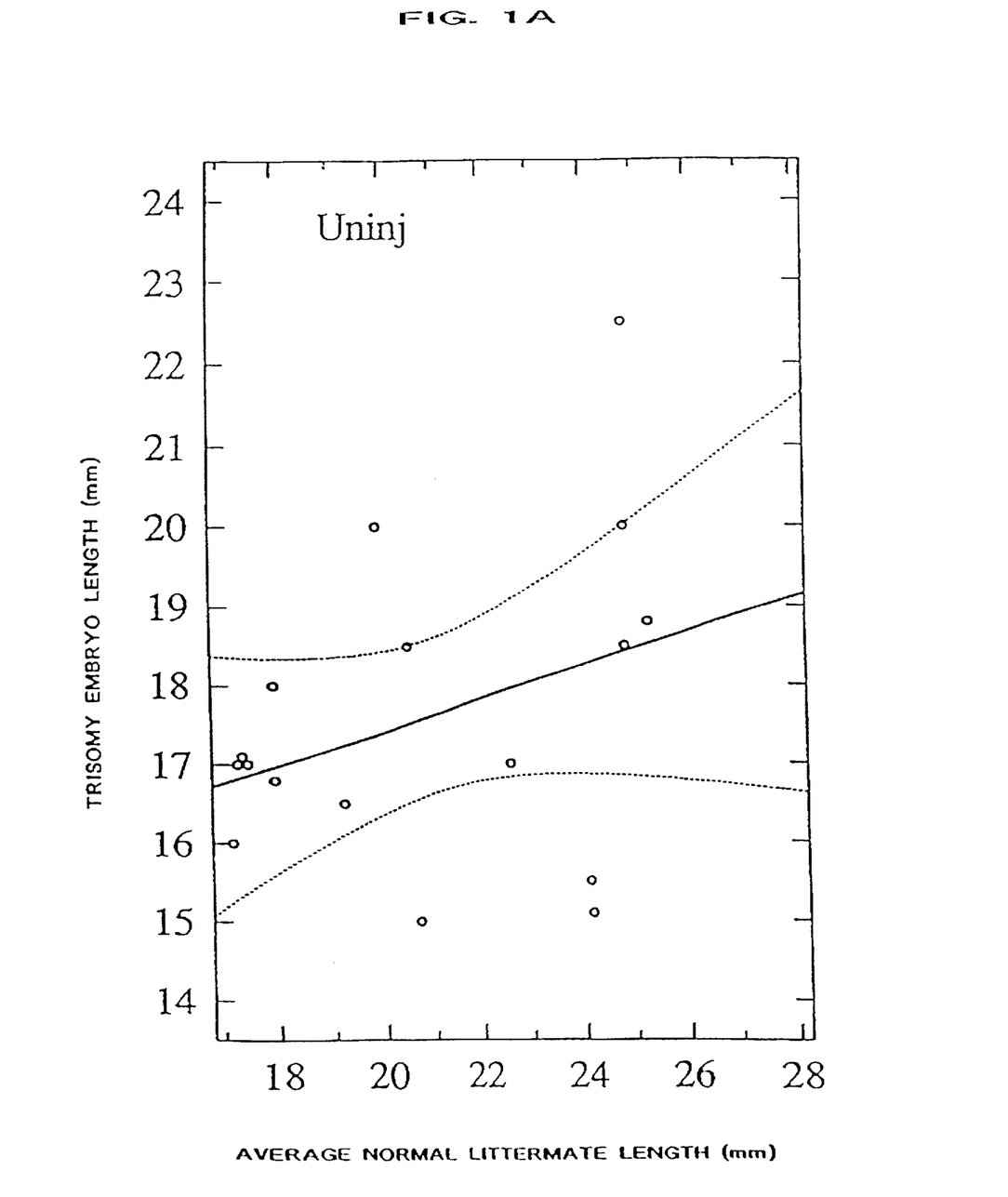
FIG. 1A, Uninjected controls.
Figure 1B:
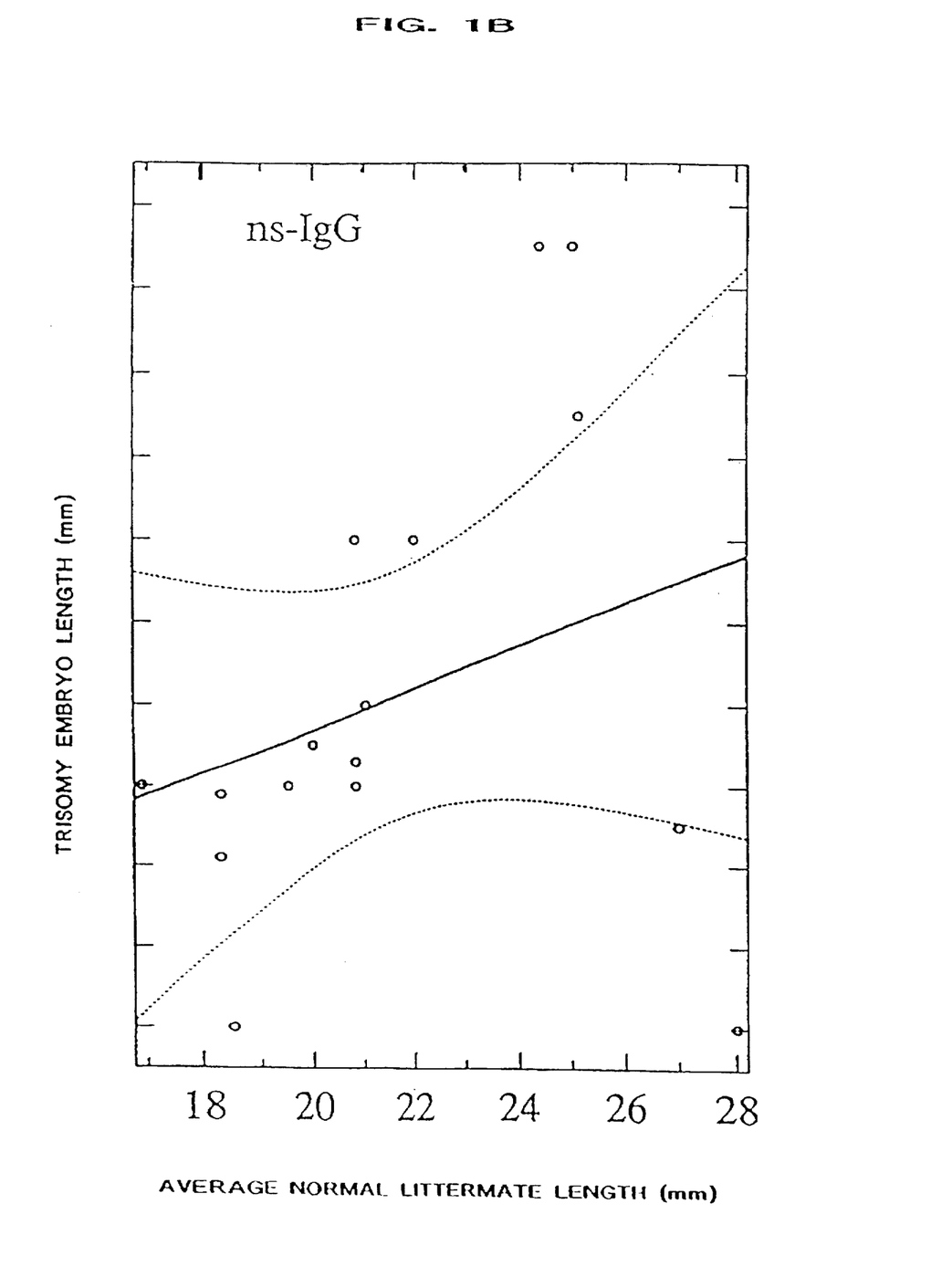
FIG. 1B, non-specific IgG (ns-IgG) injected controls.
Figure 1C:
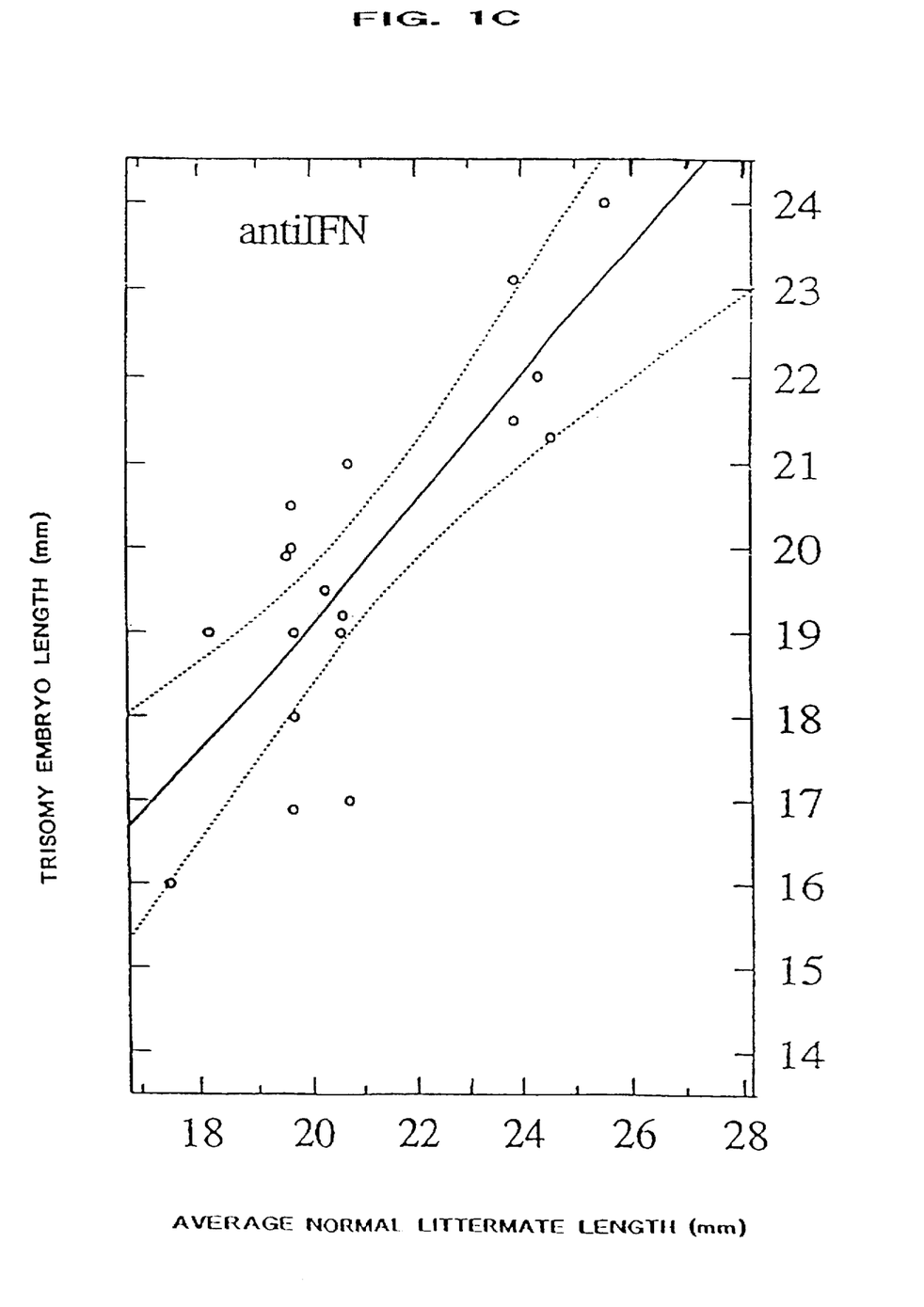

Growth Retardation. The growth retardation seen in the trisomy 16 fetus is quite variable. Nonetheless, the trisomic fetuses from the anti-IFN treated mothers showed a significant return-toward-normal growth when CRL length is plotted against the average length of the euploid littermates (FIG. 1). This analysis suggests that unlike the erratic growth of their counterparts from untreated mothers, the trisomy 16 fetuses from anti-IFN treated mothers were nearly keeping pace with the growth of their euploid littermates.

On average the trisomic fetuses from anti-IFN treated mothers showed a 5.6% decrease in length compared to a 15.28% decrease for the fetuses from non-specific IgG injected mothers (p=0.014 |0.0009|) and a 14.59% decrease for the fetuses from uninjected mothers (p=0.015 |0.010|). The two control groups were not statistically different from each other (p=0.879 |0.759|). The improvement in growth was seen consistently against both control groups and in all the fetus size groups (17–20 mm, 20–23 mm, >23 mm, Table 1).

A similar return-toward-normal growth was observed when the decrease in trisomy 16 fetal weights were analyzed. The fetuses from anti-IFN treated mothers had a mean weight decrease of −10.92% compared to a −21.47% decrease for the uninjected group (p=0.079 |0.095|, NS) and a −30.46% decrease for the ns-IgG injected group (p=0.0003 |0.0026|). The two control groups were not statistically different from each other (p=0.174 |0.33|).

There were no detectable effects of the non-specific IgG or anti-IFN injections on the euploid fetuses. Growth of each trisomic fetus was measured against its normal littermates to avoid errors due to a missed estimate of gestational age. In these matings, the mean normal littermate length (MNLL) measured 17.17 mm CRL at gestational day 16.5, 19.39 mm CRL at day 17.5 and 23.94 mm CRL at day 18.5 (plug date=day 0.5 |Kaufman' 92|). There was no significant difference between the MNLL of the uninjected control group (gestational day) 18.5 (MNLL=23.944 |N=18, p=0.419|) or the IgG injected control group (MNLL=23.75 |N=6, p=0.706|), and the anti-IFN treated group (MNLL= 23.333 |N=24|). There was also no significant difference between the MNLL of the two control groups (p=0.826).

Figure 2A:
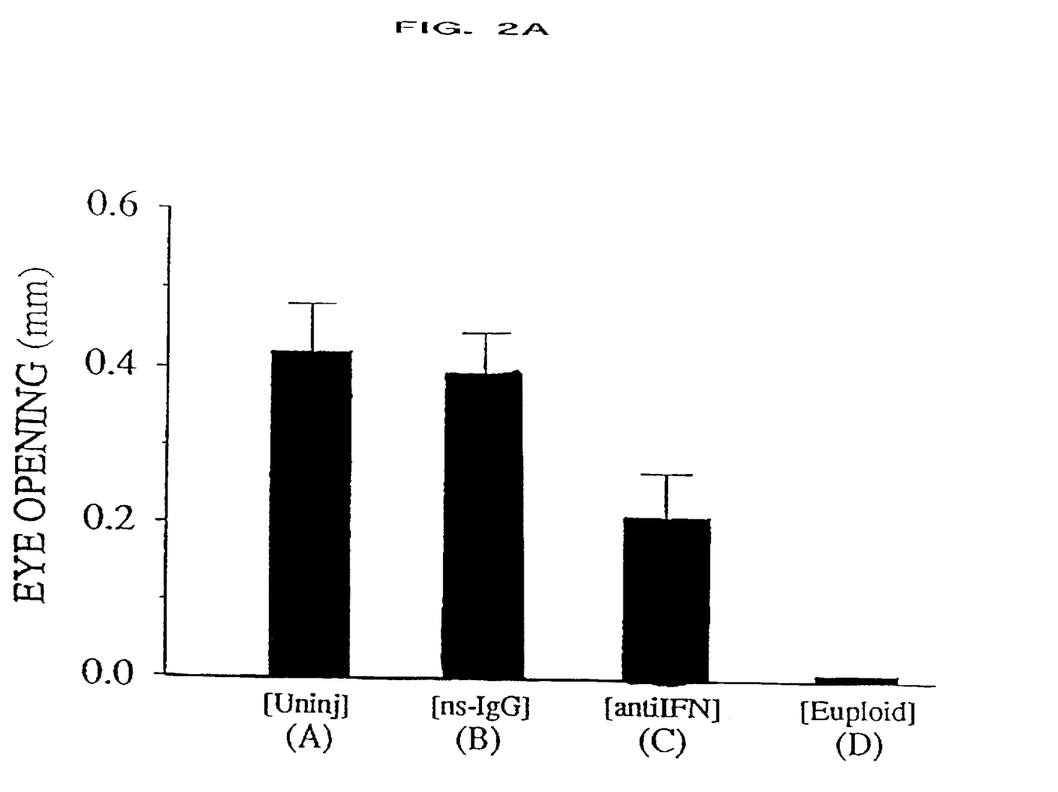
FIG. 2A, average eye opening of 17 to 23 mm trisomy 16 fetuses.

Eye Opening. Eye opening comparisons (FIG. 2A) were limited to fetuses from litters 17 mm to 23 mm in length. Prior to this stage all fetuses have open eyes. The eyes of fetuses from litters measuring 16.9–22.6 mm CRL obtained from anti-IFN treated mothers (N=13, mean=0.21 mm) had made significantly more progress toward closure than the eyes of comparably staged fetuses from untreated (N=11, mean=0.42 mm, p=0.019 |0.010|) and non-specific IgG injected mothers (N=11, mean=0.40 mm, p=0.026 |0.046|). There was no significant difference in the eye openings of the uninjected and non-specific IgG injected control groups (p=0.746 |0.300|). Progress toward eye closure may be an all or nothing event. Thus, it may be equally significant that 7 of the 13 fetuses (54%) from anti-IFN treated mothers had eye openings that averaged less than 0.2 mm compared to 2 of 11 (18%) of those from untreated mothers and 2 of 11 (18%) of the comparable fetuses from non-specific IgG treated mothers.

There have been numerous mutations detected in the mouse that lead to open eyelids (Teramoto, S, et al., 1988, Exp. Anim., 37:455–462). Most of these mutations show complete penetrance. However, some affect each eye variably and at least one phenotype can be reversed by a single maternal injection of steroids (Watney, M. J., & J. R. Miller, 1964, Nature 202:1029–1031). In addition, phenocopies of these mutants can be induced by common teratogens (Juriloff, D. M., et al., 1982 Can. J. Genet. Cytol., 25:246–254). The eyelid is lined with an active zone of cell growth (Kaufman, M. H., 1992, In: *The Atlas of Mouse Development*. Academic Press, Harcourt Brace Jovanovich, San Diego, Calif.), and these data indicate that the effect of the anti-IFN antibodies is to block cell growth inhibition of the interferon super-sensitive trisomy 16 cells lining the eyelids.

Figure 2B:
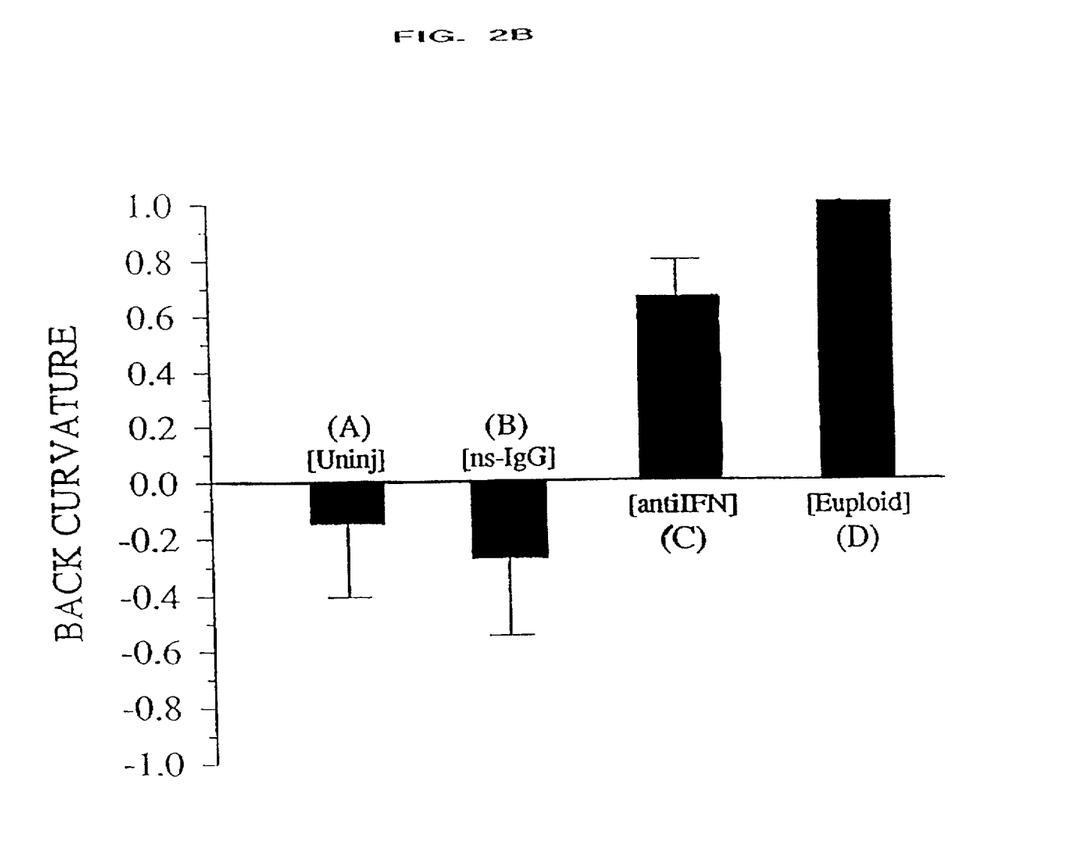
FIG. 2B, average back curvature scores of trisomy 16 fetuses greater than 20 mm in length. Columns: (A) Uninjected; (B) non-specific IgG injected; (C) anti-IFN injected; (D) euploid. The mean±standard error is presented.

Back Curvature. One of the most striking effects of the maternal anti-IFN treatment was the return-toward-normal of the curvature of the trisomy 16 fetus back which is frequently rounded at later stages where a concave curvature is expected. Back curvature comparisons (FIG. 2B) are restricted to fetuses from litters greater than 20 mm in length because both euploid and trisomic fetuses are expected to have rounded backs prior to the 20 mm stage (Theiler, K., 1972, In: *The House Mouse*. Springer, Berlin, Heidelberg, N.Y.). Back curvature was assessed by a double-blind study in which three individuals scored a rounded back as a −1, a flat back as a 0 and a convex (normal) back as a +1. There was good agreement between the scores of the three individuals (correlations ranged from 0.80 to 0.92). The mean of the three evaluations was used for comparisons.

There was no significant difference in the back curvature scores of the trisomic fetuses from uninjected and non-specific IgG injected control mothers (p=0.8236 |0.3424|). The trisomic fetuses from anti-IFN treated mothers (N=10, mean=+0.66) showed a significant return-toward-normal back curvature when compared to fetuses from untreated mothers (N=9, mean=−0.18, p=0.009 |0.009|) and the comparable fetuses from non-specific IgG treated animals (N=11, mean=−0.27, p=0.008 |0.003|).

One hundred fifty fetuses whose eyes, back, and length, appeared normal were also karyotyped (75 control and 75 anti-IFN treated). A 24 mm fetus was one of two fetuses discovered to be trisomy in this screen. A second fetus (10 mm CRL) was also found in a litter from an anti-IFN treated mother and was essentially indistinguishable from its euploid littermates. LEGEND, TABLE 1: Compilation of data on karyotyped trisomy 16 fetuses.

(A) Mean length of normal littermates (mm, CRL); (B) Length of trisomic fetus (mm, CRL); (C) Change in trisomic fetus length relative to its normal littermates (%); (D) Average weight of normal littermates (gm); (E) Weight of trisomy fetus (gms); (F) Opening of the eyes (mm); (G) Average back curvature scores of three individuals, +1=normal concave, 0=flat, −1=rounded.

7. EXAMPLE CONSTRUCTION OF A RECOMBINANT INTERFERON ANTAGONIST COMPRISING HUMAN INTERFERON α/β AND γ RECEPTOR DOMAINS

A gene encoding a fusion protein is constructed using a Glutamine-S-transferase containing expression plasmid pAcGHLT-B (Pharmingen). The interferon binding domain of the human α/β interferon receptor is obtained by Nco I endonuclease digestion of plasmid p23, available from deposit No. ATCC 65007, and isolation of the 1177 bp fragment. This fragment is inserted into the Nco I site of pAcGHLT-B to yield pAcGST-23. The interferon binding domain of the human γ interferon receptor is obtained by Dsa I and Nsp I endonuclease digestion of the plasmid pUCLGRIF16, available from deposit No. ATCC 59873, and isolation of the 603 bp fragment. A Pst I-Sma I digest of pAcGST-23 is used to remove a portion of the multiple cloning site located 3' of the gene encoding the α/β interferon receptor domain and the Dsa I/Nsp I fragment of pUCLGRIF16 is inserted to yield pAcGST-23-γr. The translation product of the resultant construct, GST-α/β-γ, contains the following domains: GST-thrombin protease site-15 amino acid leader-α/β interferon receptor domain-6 amino acid spacer-γ interferon receptor domain.

A recombinant baculovirus is constructed containing the pAcGST-23-γr operably linked to the polyhedrin promoter, suitable host cells are infected and the resultant fusion protein isolated by an anti-GST affinity absorption techniques well known in the field. See, e.g., U.S. Pat. No. 4,745,071 and U.S. Pat. No. 4,879,236 to Smith et al. The isolated fusion protein is hydrolyzed with thrombin to yield the recombinant α/β-γ receptor.

The present invention is not to be limited in scope by the specific embodiments described which were intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. All references are hereby incorporated by reference in their entirety.

2. A method of ameliorating or preventing the pathological effects of Down syndrome, which comprises administering an amount of an interferon antagonist to a human having or at risk of having Down syndrome, said amount being effective to amerliorate or prevent the pathological effects of Down syndrome, wherein the pathological effects are the result of increased responsiveness to interferon.

3. The method of claim 2 wherein the human is a human fetus.

4. The method of claim 2 wherein the human is a human infant.

5. The method of claim 2 wherein the human is a human adult.

6. The method of claim 2 wherein the interferon antagonist binds to interferon and wherein the amount of antagonist is effective to reduce the level of bioavailable interferon in the subject's blood to at most one third of a normal level of bioavailable interferon.

7. The method of claim 6 wherein the interferon antagonist is an antibody to interferon or interferon receptor and the administration is by an intramuscular, subcutaneous or intravenous route.

8. The method of claim 6 wherein the interferon antagonist is an antibody to interferon or interferon receptor and the administration is by an intramuscular, subcutaneous or intravenous route.

9. The method of claim 6 wherein the interferon antagonist comprises an interferon-binding domain of an interferon receptor and the administration is by an intramuscular, subcutaneous or intravenous route.

10. The method of claim 6 wherein the interferon antagonist comprises an interferon-binding domain of an interferon receptor and the administration is by an transplacental route.

11. The method of claim 2 wherein the antagonist blocks the action of an interferon receptor.

12. The method of claim 2 wherein the interferon antagonist is a peptide that occupies the interferon-binding domain of an interferon receptor but does not activate the interferon receptor.

TABLE 1

| Un-injected | Ln NLM (mm)[N] | (A) Ln Tri (mm)[N] | (B) % ↓ (mean ± sem) | (C) Wt NLM (gm)[N] | (D) Wt Tri (gm)[N] | (E) eyes (mm) ± sem [N] | (F) Back curv. (euploid = + 1) | (G) |
|---|---|---|---|---|---|---|---|---|
| 17–20 mm | 18.32[5] | 17.29[8] | −4.12 ± 1.7 | 0.60[5] | 0.486[8] | 0.490 ± 0.03[8] | −0.207 | 62 fetuses (17 trisomic), |
| 20–23 mm | 21.26[3] | 16.83[3] | −20.67 ± 5.5 | 0.84[3] | 0.591[3] | 0.237 ± 0.12[3] | + 0.333 | 5 resorption sites, 13 litters |
| >23 mm | 24.63[5] | 18.40[6] | −25.50 ± 4.3 | 1.21[5] | 0.749[6] | 0.200 ± 0.06[6] | −0.443 | (mean litter size: 4.8) |
| ns-IgG | | | | | | | | |
| 17–20 mm | 18.30[4] | 16.20[5] | −11.20 ± 4.0 | 0.614[4] | 9.463[5] | 0.530 ± 0.03[5] | −0.266 | 60 fetuses (16 trisomic), |
| 20–23 mm | 20.96[4] | 18.30[6] | −12.60 ± 2.2 | 0.796[4] | 0.526[6] | 0.283 ± 0.04[6] | −0.220 | 2 resorption sites, 13 litters |
| >23 mm | 25.90[5] | 19.80[5] | −22.60 ± 9.2 | 1.460[5] | 0.911[5] | 0.127 ± 0.04[5] | −0.334 | (mean litter size: 4.6) |
| Anti-IFN | | | | | | | | |
| 17–20 mm | 18.92[5] | 18.66[8] | −2.80 ± 2.4 | 0.50[5] | 0.657[8] | 0.230 ± 0.06[8] | −0.165 | 70 fetuses (18 trisomic), |
| 20–23 mm | 20.57[4] | 19.14[5] | −7.10 ± 3.2 | 0.78[4] | 0.643[5] | 0.176 ± 0.06[5] | ± 0.530 | 4 resorption sites, 13 litters |
| >23 mm | 24.59[4] | 22.38[5] | −8.40 ± 1.7 | 1.24[4] | 1.060[5] | 0.035 ± 0.03[5] | ± 0.800 | (mean litter size: 5.4) |

What is claimed is:

1. A method of ameliorating the pathological effects of a trisomy of chromosome 21 which comprises administering an amount of an interferon antagonist to a mammal having a trisomy of chromosome 21 that renders the cells of the mammal hypersensitive to interferon, said amount being effective to ameliorate the pathological effects of the trisomy, wherein the patholoical effects are the result of increased responsiveness to interferon.

13. The method of claim 2 wherein the interferon antagonist is genetically engineered.

14. The method of claim 2 wherein the interferon antagonist is an antagonist of Type I interferon.

15. The method of claim 2 wherein the interferon antagonist is an antagonist of Type II interferon.

16. The method of claim 2 wherein the interferon antagonist is an antagonist of placental interferon.

* * * * *